United States Patent
Abousaleh

(10) Patent No.: US 9,234,821 B2
(45) Date of Patent: Jan. 12, 2016

(54) DEVICE FOR MONITORING SAMPLE-COLLECTION USING A PISTON PUMP

(75) Inventor: Khaled Abousaleh, Paris (FR)

(73) Assignee: PULSSAR TECHNOLOGIES, Paris (FR)

( * ) Notice: Subject to any disclaimer, the term of this patent is extended or adjusted under 35 U.S.C. 154(b) by 681 days.

(21) Appl. No.: 13/509,684

(22) PCT Filed: Nov. 8, 2010

(86) PCT No.: PCT/FR2010/052395
§ 371 (c)(1),
(2), (4) Date: Mar. 1, 2013

(87) PCT Pub. No.: WO2011/058268
PCT Pub. Date: May 19, 2011

(65) Prior Publication Data
US 2013/0145866 A1    Jun. 13, 2013

(30) Foreign Application Priority Data

Nov. 13, 2009 (FR) ..................... 09 57999

(51) Int. Cl.
*G01N 1/14* (2006.01)
*F04B 49/00* (2006.01)

(52) U.S. Cl.
CPC *G01N 1/14* (2013.01); *F04B 49/00* (2013.01); *F04B 2205/03* (2013.01)

(58) Field of Classification Search
CPC ......... B01L 3/021; B01L 3/0217; G01N 1/14; A61M 1/00; A61B 5/150236
See application file for complete search history.

(56) References Cited

U.S. PATENT DOCUMENTS

| | | | |
|---|---|---|---|
| 2,541,621 A * | 2/1951 | Thompson | 604/92 |
| 4,549,554 A * | 10/1985 | Markham | 600/566 |
| 4,624,659 A | 11/1986 | Goldberg et al. | |
| 4,698,055 A * | 10/1987 | Sealfon | 604/82 |
| 4,815,313 A * | 3/1989 | Beard | 73/1.62 |
| 4,958,622 A * | 9/1990 | Selenke | 600/578 |
| 4,995,867 A * | 2/1991 | Zollinger | 604/514 |
| 5,118,907 A * | 6/1992 | Stout et al. | 174/135 |
| 5,295,967 A * | 3/1994 | Rondelet et al. | 604/154 |
| 6,394,977 B1* | 5/2002 | Taylor et al. | 604/100.03 |
| 6,596,081 B1* | 7/2003 | Arnowitz et al. | 117/201 |
| 7,195,610 B1* | 3/2007 | Flachbart | 604/99.01 |
| 7,418,880 B1* | 9/2008 | Smith | 73/864.01 |
| 7,581,660 B2* | 9/2009 | Nay et al. | 222/61 |
| 7,596,988 B2* | 10/2009 | Usowicz et al. | 73/61.52 |
| 7,904,258 B2* | 3/2011 | Millet | 702/50 |

(Continued)

FOREIGN PATENT DOCUMENTS

| | | |
|---|---|---|
| EP | 0316763 A1 | 5/1989 |
| FR | 2862387 A1 | 5/2005 |
| WO | 2009024562 A1 | 2/2009 |

*Primary Examiner* — David A Rogers
(74) *Attorney, Agent, or Firm* — Browdy and Neimark, PLLC

(57) ABSTRACT

The invention relates to a device (1) for monitoring sample-collection carried out using a piston pump (3, 8) such as a syringe, characterized in that said device includes a pressure sensor (11) close to the suction and/or delivery opening (6). Said device is in particular suited for use in an analysis automaton, in particular for analyzing a blood sample. Such a sensor guarantees that the liquid to be analyzed is properly sucked up, in particular that no air is sucked up and that neither the suction or delivery sides are blocked.

10 Claims, 2 Drawing Sheets

(56) References Cited

U.S. PATENT DOCUMENTS

| | | | |
|---|---|---|---|
| 7,964,160 B2 * | 6/2011 | Zuppiger et al. | 422/500 |
| 8,216,527 B2 * | 7/2012 | Dzuong | 422/505 |
| 8,608,665 B2 * | 12/2013 | Vad et al. | 600/561 |
| 8,888,677 B2 * | 11/2014 | Beckman et al. | 600/37 |
| 2002/0198498 A1 * | 12/2002 | Porat et al. | 604/187 |
| 2003/0225371 A1 | 12/2003 | Hadzic | |
| 2011/0264033 A1 * | 10/2011 | Jensen et al. | 604/65 |

\* cited by examiner

DEVICE FOR MONITORING SAMPLE-COLLECTION USING A PISTON PUMP

The present invention relates to the field of automatic samplings carried out with a piston pump, notably a pump of the syringe type. The present invention particularly relates to the takings of a sample by an automated analysis system, notably of a blood sample.

Notably in automated blood analysis systems, a sample is taken in a tube with view to its analysis. The automated system comprises a needle, provided for plunging into the tube in order to collect the sample therefrom, and a pump. The pump generally comprises a working chamber connected to the needle through a suitable conduit system. The volume of the chamber is varied, depending on whether the intention is to suck up the taken sample or to drive it back into the tube. Generally, the taken sample remains contained in the needle, or even in a portion of the conduit system in the vicinity of the needle. A fluid, generally liquid piston is contained in the chamber and the conduit system beyond the sample. The variation of the volume of the chamber, like in a syringe, is generally insured by the displacement of a plunger slidably mounted in the chamber. The volume of the chamber then depends on the position of the piston.

It is particularly important, notably if the intention is to assay elements contained in the sample and to be sure of the sucked-up and discharged sampled volumes. The same applies for reagents which may be sucked up or discharged by identical pumping means. Verification of the volumes is generally ensured by position sensors of the plunger and/or by steps of a stepping motor which drives this plunger. However, several situations may lead to a sampling error.

In a first example, foam may be formed at the surface of the blood in the tube, or the needle made not plunge into the blood. Thus, during the sampling, air will be taken instead of the intended blood, while the plunger has moved by the provided distance.

In a second example, a clot may form in the needle or the conduit system so that the no sampling can take place. However, notably if the fluid piston consists of air, this air will expand and allow displacement of the plunger over the provided distance.

In both of these examples, by only verifying the displacement of the plunger, it is suggested that the sampling was correctly carried out, while this is not the case. Further, the sampling may be carried out correctly during part of the displacement of the plunger, and may then be interrupted for example, when the blood level in the tube becomes less than that of the needle, so that the latter no longer plunges into the blood to be sampled.

The same applies to suction or discharge of any liquid.

The object of the invention is to propose a pumping device for ensuring that a liquid intended to be sucked up or discharged by means of such a device, is actually sucked up or discharged.

According to the invention, such a pumping device for ensuring that a liquid is pumped, notably sucked up and/or discharged, is characterized in that it comprises a pressure tap positioned in a pumping circuit of the device. Preferably, the pumping circuit comprises a working chamber, the volume of which varies during the pumping, the pressure tap being positioned in the chamber. This pressure tap may consist of a pressure sensor forming the whole or part of a wall of said chamber.

Thus, during suction, if the measured instantaneous pressure is greater than a first predictable threshold, it may be considered that at least one portion of the air is sucked up. If, on the contrary, the pressure is lower than a second normally predictable threshold, it may be considered that there is a plug which interferes with the suction.

Also, during a discharge, if the measured instantaneous pressure is greater than a third predictable threshold, it may be considered that at least one portion of the air is discharged. If, on the contrary, the pressure is lower than a fourth normally predictable threshold, it may be considered that there is a plug which interferes with the discharge.

Advantageously, the device may comprise a suction and/or discharge orifice and the pressure tap, for example the sensor, is positioned in the vicinity of said orifice. Thus, the device is more sensitive to malfunction of the pumping, resulting from a suction or discharge fault through the pumping circuit.

According to a particular embodiment, the pumping system may comprise a pump of the syringe type, i.e. the working chamber is cylindrical and comprises a slidably and sealably mounted plunger in the chamber, so that the volume of the chamber varies depending on the position of the plunger in the chamber, the pressure tap or pressure sensor being positioned at one end of the chamber opposite to the plunger. A sensor adapted to such a device may comprise a membrane which forms an end wall of the chamber.

The device may advantageously comprise monitoring means for comparing an instantaneous pressure measured by the sensor with normal pressure conditions.

The invention also relates to an automated analysis system, notably an automated blood analysis system, comprising a device according to the invention.

Several embodiments of the invention will be described hereafter as non-limiting examples, with reference to the appended drawings, wherein.

Figure 1:
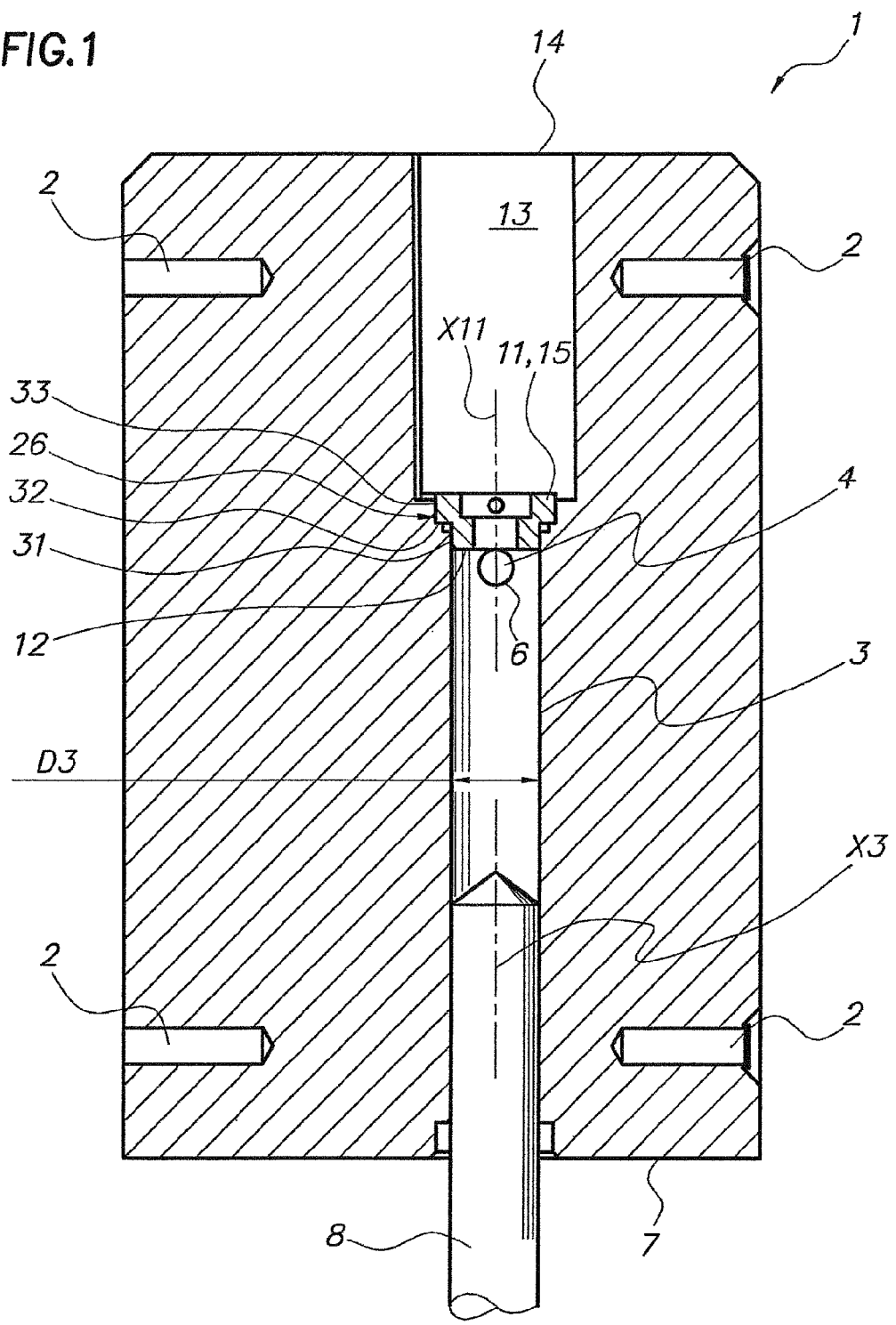
FIG. 1 is a sectional view of a pumping unit for an automated blood analysis system.

FIG. 1 illustrates a section of the pumping unit 1 intended to be mounted in an automated blood analysis system. The unit 1 is of a substantially parallelepipedal shape. It comprises bores 2 provided for mounting the unit 1 in the automated system or for its assembling with other neighbouring units. A portion 3, 4, 6 of a pumping circuit of the automated system is formed in the unit 1. This circuit portion comprises a working chamber 3 and a conduit 4 opening through an orifice 6 into the chamber 3 in the vicinity of a first end of the latter. The conduit 4 is used both for suction and for discharge.

The working chamber 3 substantially has the shape of an axisymmetrical cylinder around an axis X3 of the sectional plane of FIG. 1. The chamber 3 is open through a second end opposite to the first, through, and perpendicularly to, a first face 7 of the unit 1. The unit 1 further comprises a plunger 8 mating the chamber 3 and slidably mounted in the latter. The plunger 8 penetrates the chamber 3 through its opening in the face 7. The plunger 8 is sealably mounted with the chamber 3. The plunger is translationally driven by a stepping motor, not illustrated in the figures.

The first end of the chamber 3 is closed by a pressure sensor 11 which forms a wall 12 of the chamber 3. The end wall 12 extends over the whole transverse dimension of the chamber 3, perpendicularly to the X axis. The sensor 11 comprises a body 15 which is in particular illustrated in FIG. 2, more specifically and on a larger scale.

The conduit 6 radially extends from the chamber 3 towards a concealed face of the unit 1, opposite to the observer in FIG. 1. The orifice 6 is substantially tangent to the end wall 12. Thus, in the close vicinity of the conduit, the sensor is sensitive to the least pressure modification due to an alteration of the flow in the conduit 4 or beyond, for example if air is sucked up or if a plug is formed in the pumping circuit. Beyond conduit 6, the pumping circuit ends in a needle (not shown in the figures) provided for taking a blood sample in a suitable tube, which contains blood to be analyzed.

The unit 1 further comprises a mounting cavity 13 which opens out through a second face 14 of the unit 1, opposite to the first face 7. The cavity 13 is provided for allowing the sensor 11 to be mounted through the second face 14 of the unit 1.

The mounting cavity 13 and the working chamber 3 form together a housing 26 for the sensor 11. The housing is axisymmetrical around the axis X3 of the chamber 3. Depending on whether one proceeds from chamber 3 to the cavity 13, the housing comprises 3 successively larger cylindrical areas 31-33 each separated from the next by a ring-shaped shoulder 34,35. The first cylindrical area 33 with a constant diameter D3 extends the working area 3. The diameter D32 of the second area 32 and the diameter D33 of the third area 33 are such that D33>D32>D31. The ring-shaped shoulders 34,35 are perpendicular to the axis X3.

Figure 2:
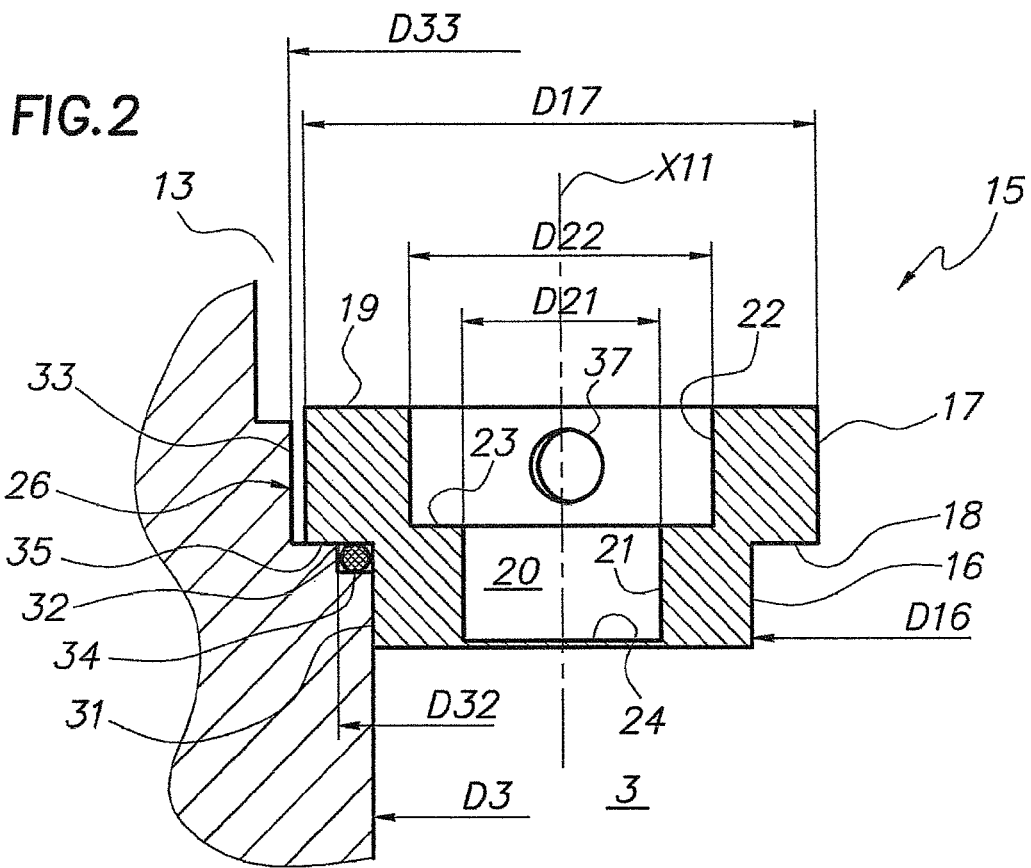
FIG. 2 is a view of a section of a body for a pressure sensor with which the unit of FIG. 1 is equipped, and of a left half section of the unit in the vicinity of the body; and, FIG. 3 is a curve illustrating a predictable pressure of versus the sucked-up volume.

The body 15 will now be described with reference to FIG. 2.

The body 15 is of a substantially axisymmetrical shape around an axis X11, provided so as to coincide with the axis X3 of the chamber, when the sensor 11 is mounted in the unit 1.

The body 15 is exteriorly defined by a solid front face 12, two cylindrical lateral surfaces 16,17 forming together a ring-shaped shoulder 18, and a ring-shaped rear surface 19.

The body 15 comprises an inner space 20 defined by two cylindrical inner surfaces 21,22 forming together a ring-shaped shoulder 23.

The shoulders and the front and rear faces are in respective planes perpendicular to the axis X11.

The body 15 further comprises a measurement channel 37, which opens out into the inner space 20, and is intended to be put into communication with an instrument (not shown in the figures) for measuring pressure in the space 20.

The front face 12 is provided for forming the end wall 12 of the working chamber 3. The front face 12 is essentially formed by a deformable membrane 24 depending on the pressure difference between the working chamber 3 and the inner space 20 of the body 15 of the sensor 11. The use of such a membrane 24 is particularly advantageous. Indeed, taking into account its small size and its small displacement, the membrane 24 allows measurement of the pressure in the chamber 3 without modifying the volume thereof, therefore, without any influence on the sampled and/or distributed volume, contrary to other solutions which detect the diameter variation of a flexible pipe, other solutions for which the volume variation is substantial and notably plays a part in the actually sampled and/or distributed volume.

A first lateral surface 16 among lateral surfaces 16, 17, has a smaller diameter D16 than diameter D17 of the second surface 17. The diameter D16 is substantially equal to the diameter D3 of the chamber 3, so that the first lateral surface 16 will fit into the first area 31 of the housing 26, with adjustment. The diameter D17 of the second outer surface 17 is larger than the diameter D32 of the second area 32 of the housing 26; it is also smaller than the diameter D33 of the third area 33 of the same housing 26. Thus, when the sensor 11 is mounted on the unit 1, i.e. the body is in the position illustrated in FIGS. 1 and 2, the shoulder 18 of the body bears against the second shoulder 35 of the housing 25, thereby defining the position of the wall 12 of the chamber 3. In the second area 32 of the housing 26, a ring-shaped space is defined between the first shoulder 34 and the outer shoulder 18 of the body 15 in which an O-ring is mounted, compressed between both of these shoulders, so that it ensures the when a blood sample is sucked up. This area may advantageously be determined experimentally and be recorded by learning means integrated to the automated system.

If, during suction, for a given volume V, the instantaneous pressure P is below curve C2, or above curve C1, the sampling of the sample should be considered as nil and should be performed again. Preliminary cleaning of the pumping circuit may be required, if a plug is formed therein. It may be necessary to reposition the tube containing the sample to be taken, so that the sampling needle is sufficiently plunged therein so as to not suck up any air seal of the working chamber 3.

Other elements of the sensor 11 are neither described nor illustrated.

Figure 3:
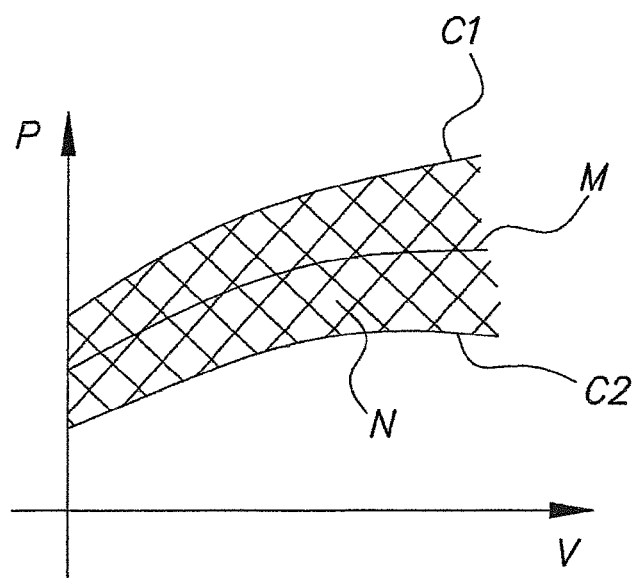

FIG. 3 illustrates a curve of the pressure P, measured by the sensor 11, versus the volume V of the chamber 3 at a given instant, during suction. A volume V corresponds to a given instantaneous position of the plunger 8 in the chamber 3. This curve is purely illustrative, it notably varies according to the dimensions of the chamber, to the speed of the piston in the chamber and to the viscosity of the fluid to be sampled.

A hatched area N, limited by an upper curve C1 and a lower curve C2, around a median theoretical curve M. This area N represents normal operating conditions As an example, such a device may notably have the following dimensions:

D3 #D16=6 mm

D17=8 mm

Of course, the invention is not limited to the examples which have just been described.

Thus, the pump may be of a type other than the syringe type, i.e. including a piston sliding in a cylindrical chamber, as illustrated in the figures.

Also, the device may not be in the form of a unit, but may comprise individualized elements. Further, a device according to the invention may advantageously comprise control means, for example, a processor, and memory means, for notably carrying out the whole or part of the following functions:

- building up by learning, a database illustrating normal or abnormal pressure conditions during pumping;
- recording and storing such a database;
- instantaneous comparison of pumping pressures with the data from the base;
- warning issued in the case of abnormal instantaneous pressure values.

The invention claimed is:

1. A pumping device (1) for an automated analysis system, with which it is possible to ensure that a liquid is pumped, notably sucked up and/or discharged, comprising:
   - a working chamber (3), the volume of which varies during pumping,
   - a slidably and sealably mounted plunger (8) movably inserted in a first end of the working chamber so that the volume of the chamber varies according to the position of the plunger in the chamber,
   - a pressure tap (11) positioned at a second end of the working chamber (3) opposite to the first end, and forming at least a part of an end wall of the working chamber, an orifice (6) defined in a longitudinal wall of the working chamber, the orifice defined so as to be substantially tangent to the pressure tap (11), and a conduit (4) opening through the orifice (6) into the chamber (3) through which suction can be applied.

2. The device according to claim 1, wherein the pressure tap comprises a pressure sensor (11).

3. The device according to claim 1, wherein the sensor (11) comprises a membrane (24) which forms an end wall (12) of the chamber (3).

4. The device according to claim 1, further comprising a monitor for comparing and instantaneous pressure measured by the sensor with normal pressure conditions.

5. The device according to claim 1, wherein said pressure tap (11) comprises a body (15), the body having a first section having a first diameter substantially equal to a diameter of the working chamber (3), and a second section having a second diameter larger than the first diameter, the first section extending from the first section and the first section configured to be inserted into the working chamber.

6. The device according to claim 5, further comprising a housing having a through bore extending therethrough from a first surface to a second surface opposite to the first surface, the through bore having a first section opening at the first surface, and a second section opening at the second surface, the first section having a smaller diameter than a diameter of the second section, and the second section having a larger diameter than the second diameter of the second section of the body.

7. The device according to claim 1, further comprising a housing having a through bore, wherein the pressure tap (11) comprises a first lateral surface (16) and a second lateral surface (17), the first lateral surface having a diameter smaller than a diameter of the second lateral surface, the diameter of the first lateral surface being substantially equal to a diameter of the working chamber (3), so that the first lateral surface will fit into a first area of the through bore of housing (26).

8. The device according to claim 7, wherein the second lateral surface of the pressure tap has a second diameter larger than a second area of the through bore of the housing, and the second diameter of the second lateral surface is smaller than a third diameter of the through bore of the housing, such that when the pressure tap is inserted in the though bore of the housing, a first shoulder of the body bears against a first shoulder of the bore, thereby defining a position of the wall of the chamber.

9. The device according to claim 8, further comprising an O-ring mounted in a ring-shaped space defined between the first shoulder and the second shoulder of the through bore, such that the O-ring is compressed between the first and second shoulders.

10. An automated analysis system, notably for blood analysis, comprising a device according to claim 1.

* * * * *